United States Patent
Kuo et al.

(10) Patent No.: US 10,072,039 B2
(45) Date of Patent: Sep. 11, 2018

(54) PROCESS FOR THE PRODUCTION OF FONDAPARINUX SODIUM

(71) Applicant: Scinopharm Taiwan, LTD., Shan-Hua, Tainan (TW)

(72) Inventors: Lung-Huang Kuo, Tainan (TW); Shang-Hong Chen, Chiayi (TW); Li-Ting Wang, Tainan (TW); Wen-Li Shih, Nantou (TW); Yuan-Xiu Liao, Tainan (TW)

(73) Assignee: ScinoPharm Taiwan, Ltd. (TW)

( * ) Notice: Subject to any disclaimer, the term of this patent is extended or adjusted under 35 U.S.C. 154(b) by 181 days.

(21) Appl. No.: 13/950,745

(22) Filed: Jul. 25, 2013

(65) Prior Publication Data
US 2015/0031866 A1 Jan. 29, 2015

(51) Int. Cl.
*C07H 1/00* (2006.01)
*C07H 15/04* (2006.01)

(52) U.S. Cl.
CPC ............... *C07H 15/04* (2013.01); *C07H 1/00* (2013.01)

(58) Field of Classification Search
None
See application file for complete search history.

(56) References Cited

U.S. PATENT DOCUMENTS

| | | | |
|---|---|---|---|
| 4,818,816 A | 4/1989 | Petitou et al. | |
| 7,541,445 B2 * | 6/2009 | Seifert et al. | 536/21 |
| 8,288,515 B2 | 10/2012 | Nadji et al. | |
| 9,346,844 B2 | 5/2016 | Kuo et al. | |
| 2005/0020536 A1 | 1/2005 | Branellec et al. | |
| 2009/0187013 A1 | 7/2009 | Seifert et al. | |
| 2011/0105418 A1 * | 5/2011 | Nadji et al. | 514/25 |
| 2011/0306757 A1 | 12/2011 | Lopez-Belmonte Encina et al. | |
| 2012/0116066 A1 | 5/2012 | Patel et al. | |
| 2012/0208993 A1 | 8/2012 | Seifert et al. | |
| 2013/0005954 A1 | 1/2013 | Kovi et al. | |
| 2015/0031865 A1 | 1/2015 | Kuo | |

FOREIGN PATENT DOCUMENTS

| | | |
|---|---|---|
| CA | 1265132 A | 1/1990 |
| CN | 103122012 A | 5/2013 |
| JP | 5-331182 A | 12/1993 |
| JP | 2010-517998 A | 5/2010 |
| WO | WO-2008/094054 A2 | 8/2008 |
| WO | WO-2008/094054 A3 | 8/2008 |
| WO | 2013115817 A1 | 8/2013 |
| WO | 2015011517 A1 | 1/2015 |
| WO | 2015011519 A1 | 1/2015 |

OTHER PUBLICATIONS

Manikowski, A. et al., Carbohydrate Research, "An Alternative Route for Fondaparinux Sodium Synthesis via Selective Hydrogenations and Sulfation of Appropriate Pentasaccharides", Sep. 2012, vol. 361, pp. 155-161.*
Gilbert, E. E., Chem. Rev. 62, 6, 549-589 (Year: 1962).*
U.S. Appl. No. 13/950,716, filed Jul. 25, 2013.
PCT Application No. PCT/IB2013/002376, International Search Report and Written Opinion, dated Apr. 24, 2014, 7 pages.
PCT Application No. PCT/IB2013/002161, International Search Report and Written Opinion, dated Apr. 23, 2014, 10 pages.
Codée, Jeroen D.C. et al., "A Modular Strategy Toward the Synthesis of Heparin-like Oligosaccharides Using Monomeric Building Blocks in a Sequential Glycosylation Strategy," *J. Am. Chem. Soc.* (2005) 127:3767-3773.
Ganguli, Anjali R. S. et al., "αβ Selectivity in the synthesis of 3-substituted, 4-methyl umbelliferone glycosides of N-acetyl glucosamine and chitobiose," *Assymetry* 16 (2005) 411-424.
Weisstein, "Ratio," From MathWorld—A Wolfram Web, Resource, http://mathworld.wolfram.com/radio.html, viewed Aug. 2015.
Koziol, A. et al., "A Fast and Effective Hydrogenation Process of Protected Pentasaccharide: A Key Step in the Synthesis of Fondaparinux Sodium," Org Process Res Dev 17(5):869-875, (May 17, 2013, e-published Apr. 18, 2013).
Lin, F. et al., "Synthesis of Fondaparinux: modular synthesis investigation for heparin synthesis," Carbohydr Res 371:32-39, (Apr. 19, 2013, e-published Jan. 16, 2013).
Ichikawa, Y. et al. (Sep. 1, 1985). "Synthesis, from cellobiose, of a trisaccharide closely related to the GlcNAc----GlcA----GlcN segment of the antithrombin-binding sequence of heparin," *Carbohydr Res* 141(2):273-282.
Schrickel, J. (2010). "Sulfur Trioxide Amine Complexes: Versatile Reagents in Organic Synthesis," presented at RSC Symposium Berlin 2010, CABB, 16 pages.

* cited by examiner

*Primary Examiner* — Shaojia A Jiang
*Assistant Examiner* — Bahar Craigo
(74) *Attorney, Agent, or Firm* — Mintz Levin Cohn Ferris Glovsky and Popeo PC

(57) ABSTRACT

The present invention provides improved processes of preparing Fondaparinux sodium comprising converting a compound of formula ABCDE4 to Fondaparinux sodium at a reaction pH of no more than about 9.0. In some embodiments, the intermediates for the synthesis of Fondaparinux sodium, are also provided.

4 Claims, No Drawings

PROCESS FOR THE PRODUCTION OF FONDAPARINUX SODIUM

CROSS-REFERENCES TO RELATED APPLICATIONS

Not applicable

BACKGROUND OF THE INVENTION

Fondaparinux sodium (CAS 114870-03-0) is a member of oligosaccharides/heparins with a chemical name of O-[2-Deoxy-6-O-sulfo-2-(sulfoamino)-alpha-D-glucopyranosyl]-(1-4)-O-(beta-D-glucopyranurosonyl)-(1-4)-O-[2-deoxy-3,6-di-O-sulfo-2-(sulfoamino)-alpha-D-glucopyranosyl]-(1-4)-O-(2-O-sulfo-alpha-L-idopyranurosonyl)-(1-4)-O-[2-deoxy-1-O-methyl-6-O-sulfo-2-(sulfoamino)-alpha-D-glucopyranoside]decasodium salt, which developed by Choay, S. A. (see U.S. Pat. No. 4,818,816). The compound is a synthetic pentasaccharide Factor Xa inhibitor which is indicated as an anticoagulant drug used for the prevention of deep vein thrombosis in patients who have had orthopedic surgery as well as for the treatment of deep vein thrombosis and pulmonary embolism. It was approved by the United States Food and Drug Administration in 2001, marketed under the trade name Arixtra™ which is administrated subcutaneously.

The preparation process of Fondaparinux sodium disclosed in U.S. Pat. No. 4,818,816 is unsuitable for a large scale production since this process takes over 60 steps to afford a final product with low yield.

U.S. Pat. No. 8,288,515 applies protection and de-protection steps to prepare Fondaparinux sodium. However, the de-protection step results in low yields and consumes additional reaction time.

Another process is disclosed in U.S. 2011/0306757, but the additional reduction step of an azide needs further purification and the final N-sulfonation step remains in low yield (68%).

US 2012/0116066 describes the preparation of Fondaparinux sodium and its intermediates. However, the preparation of some intermediates such as EMod3 needs column purification. Moreover, the low α/β ratios in the coupling between C monomer and D monomer as well as numerous time-consuming procedures are not optimal.

In view of the above, there is still a need for a simple process with higher yield/purity for industrial preparation of Fondaparinux sodium.

BRIEF SUMMARY OF THE INVENTION

The present invention provides an economic process to prepare Fondaparinux sodium.

In one aspect, the present invention provides a process of preparing Fondaparinux sodium comprising contacting a compound of formula ABCDE4 with a sulfur trioxide-amine complex at a reaction pH of no more than 9.0.

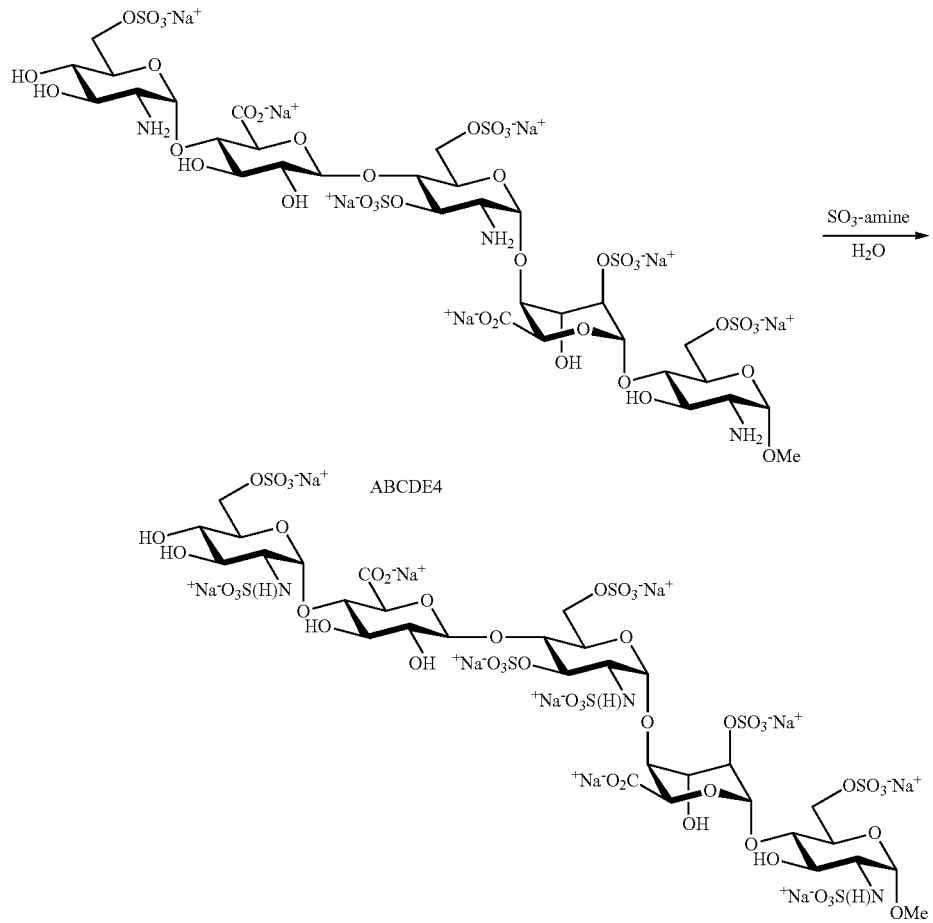

Preferably, the sulfur trioxide-amine complex is selected from the group consisting of sulfur trioxide trialkylamine complex, such as sulfur trioxide-trimethylamine complex, sulfur trioxide-triethylamine complex and sulfur trioxide-dimethylethylamine complex, sulfur trioxide-dialkylaniline complex such as sulfur trioxide-dimethylaniline complex and sulfur trioxide-dimethylformamide complex and mixtures thereof. More preferably, the sulfur trioxide-amine complex is sulfur trioxide-trimethylamine or sulfur trioxide-triethylamine complex.

Previously, when Fondaparinux was prepared using sulfur trioxide-pyridine complex ($SO_3$-Py) at pH 9-9.5 and impurities were present in the final product. See U.S. 2012/0116066. The structures of some of the impurities, such as de-sulfation impurities, are shown below in Scheme 1. Further, Fondaparinux sodium prepared by using $SO_3$-Py was a brown solid, which is not preferred in the pharmaceutical industry.

Scheme 1

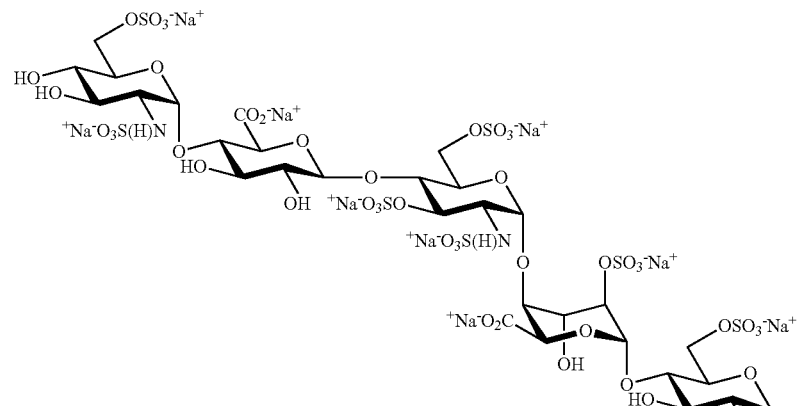

ABCDE4-2S-1

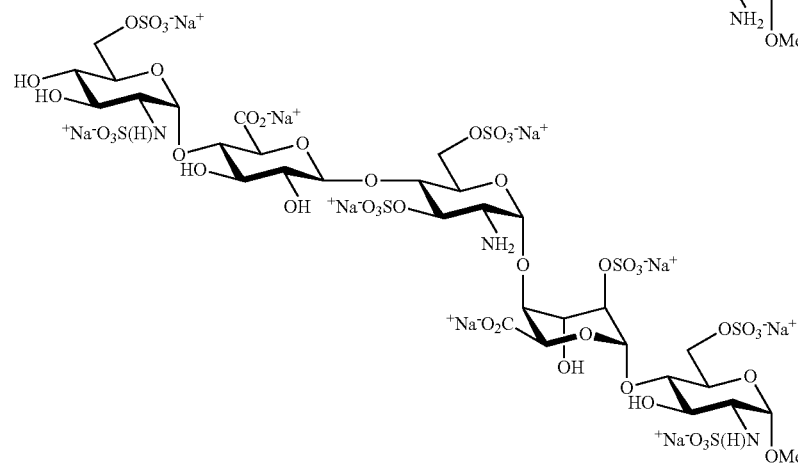

ABCDE4-2S-2

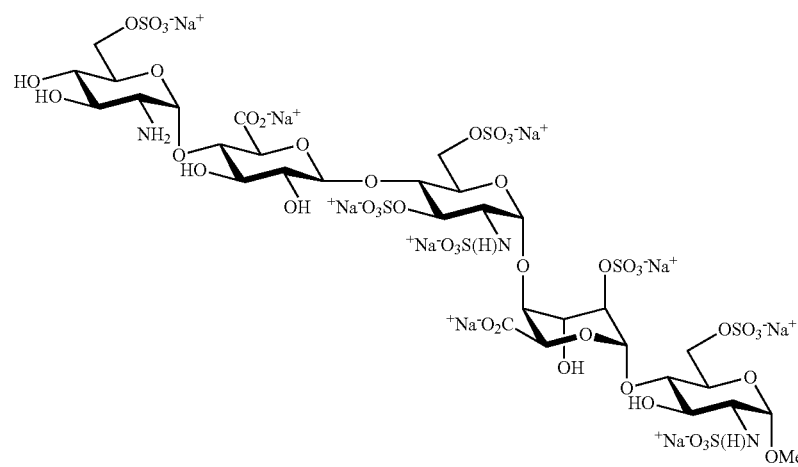

ABCDE4-2S-3

It was found that the use of sulfur trioxide-trimethylamine complex resulted in reduced impurities compared to previous methods using $SO_3$-Py and afforded Fondaparinux sodium as a white solid rather than brown one. Additionally, the use of the methods described herein reduces the occurrence of de-sulfation impurities shown in Scheme 1 above. In a group of embodiments, Fondaparinux sodium prepared using sulfur trioxide-trimethylamine complex resulted in less than about 3% of de-sulfation impurities in the final product, or less than about 2% de-sulfation impurities in the final product, preferably less than about 1.55% de-sulfation impurities in the final product.

Preferably, the sulfation reaction using sulfur trioxide-trimethylamine complex is conducted at a pH range of about 8.0 to 9.0. More preferably, the pH of the reaction mixture for the sulfation reaction using sulfur trioxide-triethylamine is 8.0. When the pH of the reaction mixture was higher than 9.0, over-sulfation of ABCDE4 was observed and the following over-sulfation impurities (ABCDE4-4S-1 to ABCDE4-4S-6, shown in Scheme 2 below) were obtained as significant impurities.

Scheme 2

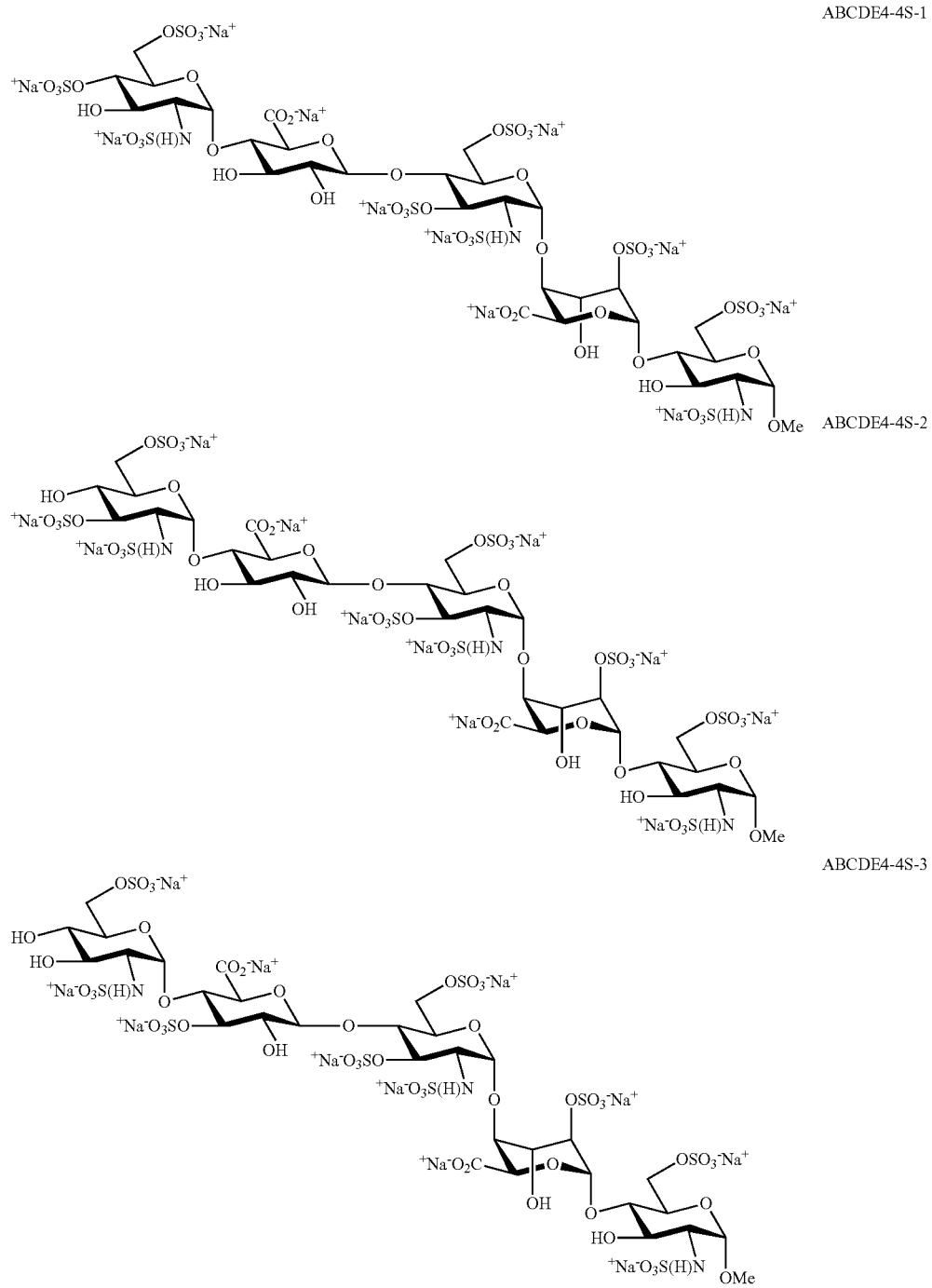

ABCDE4-4S-4

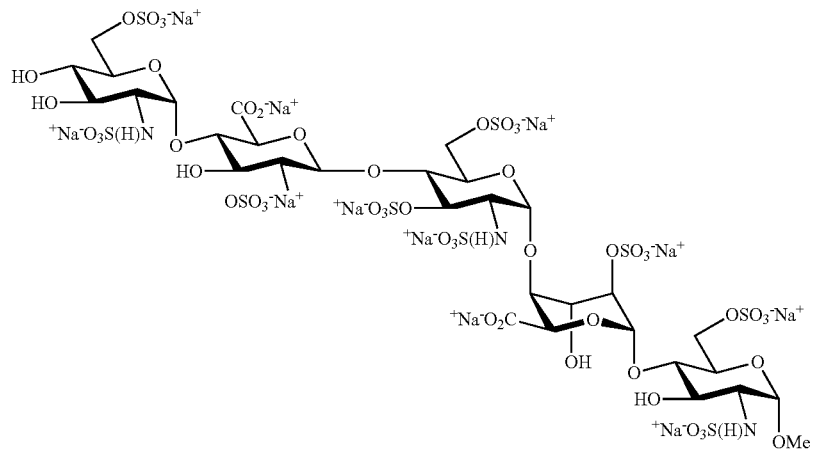

ABCDE4-4S-5

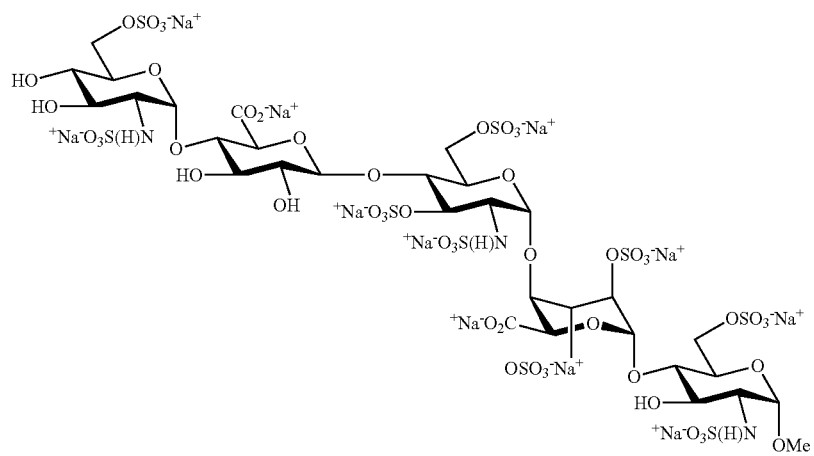

ABCDE4-4S-6

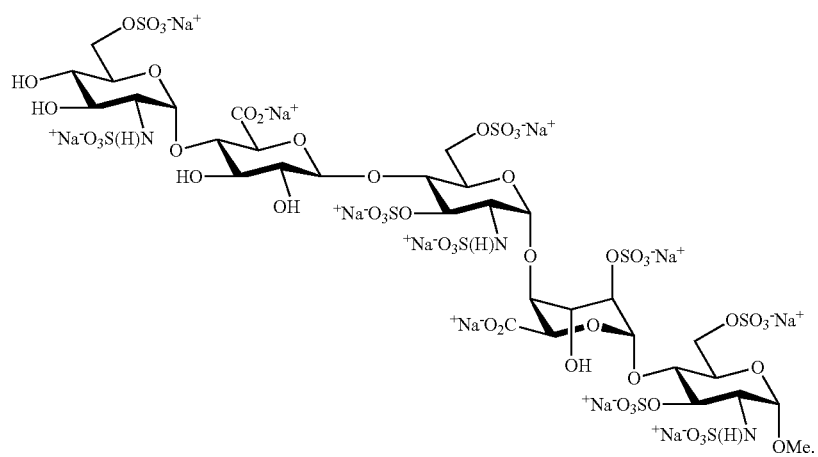

When various reaction pH ranges were compared, it was found that the total amount of over-sulfation impurities was lower (1.55%) when the reaction was conducted at pH=8.5, whereas more impurities were generated (13.37%) when the reaction was conducted at pH=10.5. Moreover, when the pH value of both ABCDE4 solution and the reaction mixture were controlled to a range of pH 8.0-9.0, the amount of impurities from over-sulfation in Fondaparinux sodium further decreased to 0.7%. Accordingly, the presently described methods decrease the impurities (including de-sulfation impurities and over-sulfation impurities) in the final Fondaparinux product. In a group of embodiments, Fondaparinux sodium prepared using sulfur trioxide-trimethylamine complex resulted in less than about 3% of over-sulfation impurities in the final product, or less than about 2% over-sulfation impurities in the final product, preferably less than about 1.55% over-sulfation impurities in the final product, more preferably less than about 1% or 0.8% over-sulfation impurities in the final product. In current process, the purity of crude fondaparinux sodium was about 90%.

Sanofi-Synthelabo reported in US2005020536 that Fondaparinux can be purified in the final step with activated charcoal to reduce the contents of the related cyclohexyl impurities shown in Scheme 3 below. By contrast, the present methods involve purification of an intermediate compound of formula ABCDE4 with activated charcoal before reacting with sulfur trioxide amine complex. The present invention applies activated charcoal to remove impurities from an intermediate, i.e., from an ABCDE4 mixture, rather than from the final product, i.e., Fondaparinux. Accordingly, the presently described methods allow for early removal of cyclohexyl impurities with activated charcoal, in advance of the sulfation step which occurs late in the synthesis, thereby further increasing the purity of the final Fondaparinux product.

Scheme 3

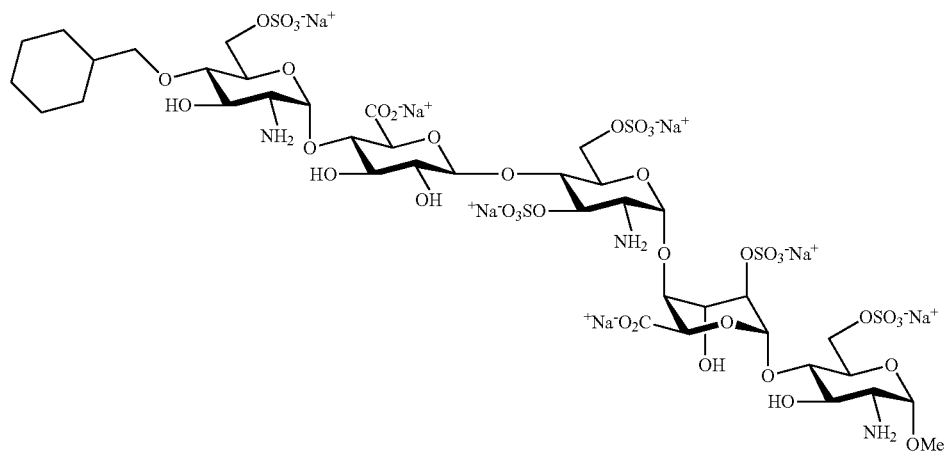

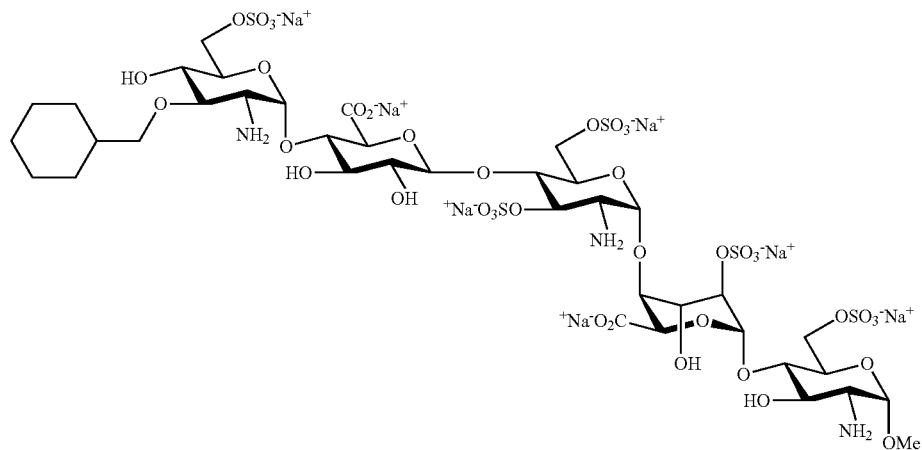

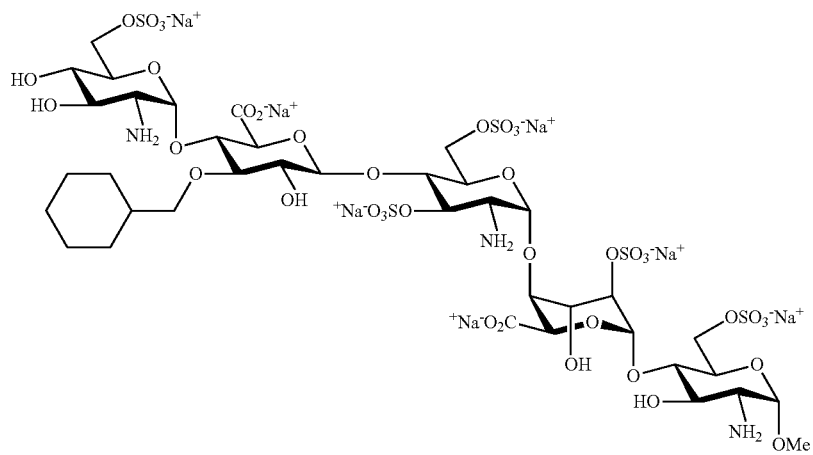

-continued

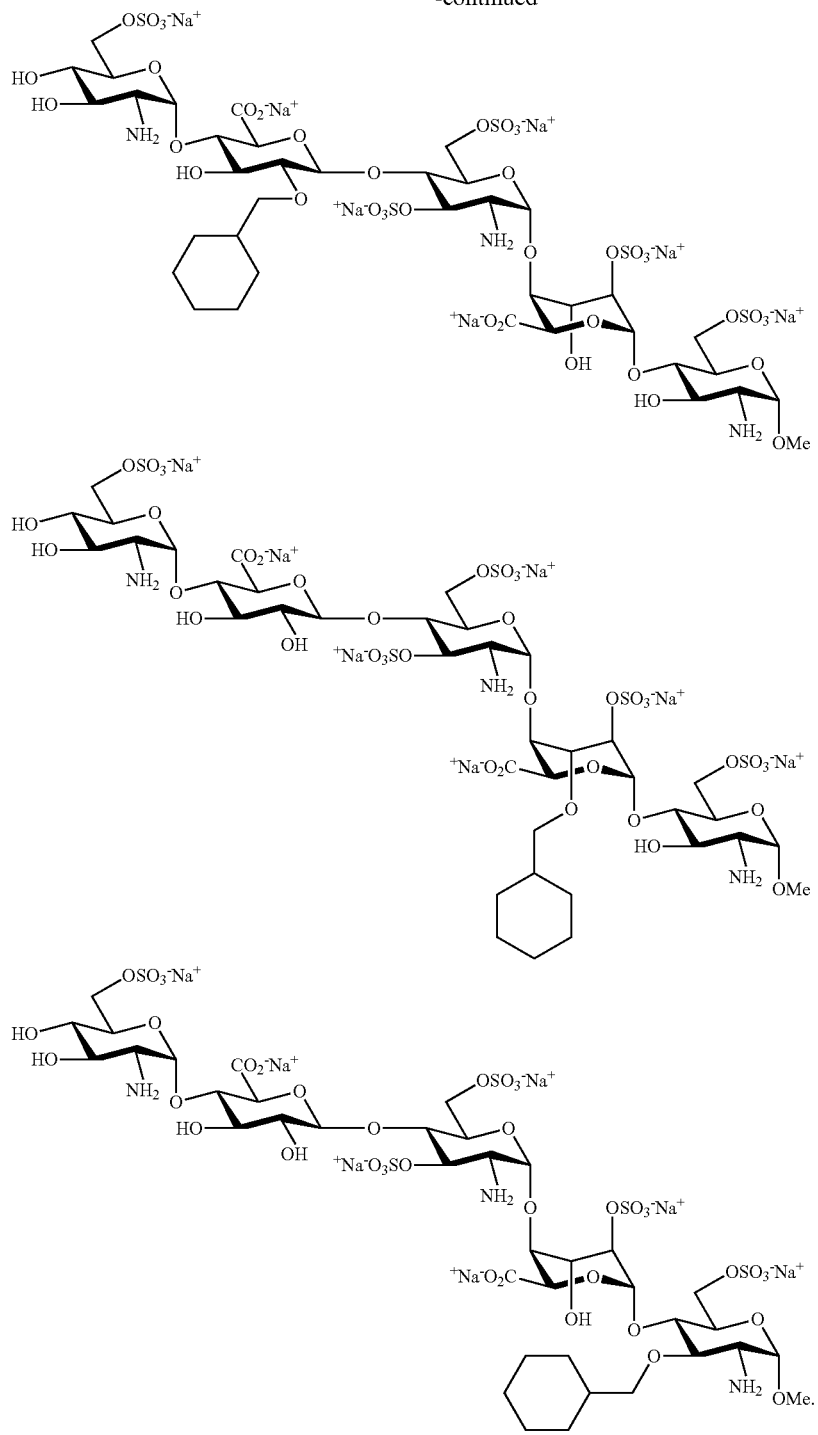

DETAILED DESCRIPTION OF THE INVENTION

I. General

The present invention provides a process for preparation of Fondaparinux sodium. The novel processes described herein afford Fondaparinux sodium in higher yield, and with less impurities. The inventive process reduces the time required for certain synthetic steps thereby reducing manufacturing costs.

II. Definitions

As used herein, the term "contacting" refers to the process of bringing into contact at least two distinct species such that they can react. It should be appreciated, however, that the resulting reaction product can be produced directly from a reaction between the added reagents or from an intermediate from one or more of the added reagents which can be produced in the reaction mixture.

As used herein, the term "alkyl" by itself or as part of another substituent, means, unless otherwise stated, a straight or branched chain hydrocarbon radical. Alkyl substituents, as well as other hydrocarbon substituents, may contain number designators indicating the number of carbon atoms in the substituent (i.e., $C_1$-$C_8$ means one to eight carbons), although such designators may be omitted. Unless otherwise specified, the alkyl groups of the present invention contain 1 to 12 carbon atoms. For example, an alkyl group can contain 1-2, 1-3, 1-4, 1-5, 1-6, 1-7, 1-8, 1-9, 1-10, 1-11, 1-12, 2-3, 2-4, 2-5, 2-6, 3-4, 3-5, 3-6, 4-5, 4-6 or 5-6 carbon atoms. Examples of alkyl groups include methyl, ethyl, n-propyl, isopropyl, n-butyl, t-butyl, isobutyl, sec-butyl, n-pentyl, n-hexyl, n-heptyl, n-octyl, and the like.

As used herein, the term 'substituted' when referring to alkyl, phenyl and benzyl, refers to one or more substituents, typically one to three substituents that are selected to be non-interfering substituents such as halogen, amino, hydroxy, nitro, cyano, lower alkyl (e.g., $C_{1-4}$ alkyl), lower alkoxy (e.g., $C_{1-4}$ alkyl-O—), lower alkylamino (e.g., $C_{1-4}$ alkyl-NH—), di-lower alkylamino (e.g., di-$C_{1-4}$ alkylamino), and haloalkyl. One of skill in the art will appreciate that additional substituted alkyl, phenyl and benzyl are known and useful in the context of the invention.

Various protecting groups and protecting reagents, including hydroxyl protecting reagents, are well known to one of ordinary skill in the art and include compounds that are disclosed in *Protective Groups in Organic Synthesis,* 4th edition, T. W. Greene and P. G. M. Wuts, John Wiley & Sons, New York, 2006, which is incorporated herein by reference in its entirety.

III. Embodiments of the Invention

The starting material ABCDE4 for the methods described herein is prepared by a series of steps as follows. Initially, ABC1 is prepared by a) converting a compound of formula A4

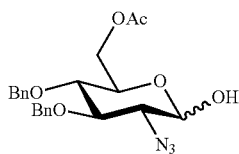

A4 to provide a compound of formula A5

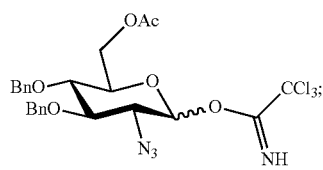

A5 and b) contacting the compound of formula A5 with a compound of formula BC8

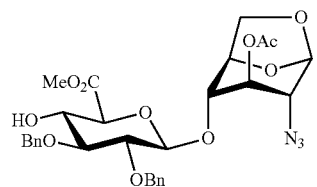

BC8 under conditions sufficient to provide a compound of formula ABC1

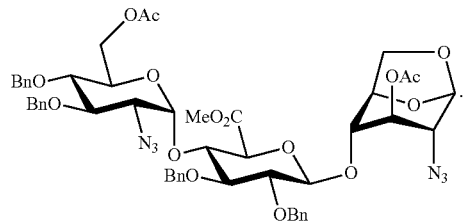

ABC1

In step (a) above, the conversion of A4 to A5 is conducted in the presence of a base and trichloroacetonitrile. In one group of embodiments the base is an organic amine (e.g., DBU, pyridine, triethylamine, diisopropylethyl amine, pyrrolidine, or any other such organic base). In another group of embodiments, the base is an inorganic base (e.g., potassium carbonate, sodium carbonate, potassium bicarbonate, sodium bicarbonate, cesium carbonate, potassium phosphate, or any other such inorganic base). A number of bases are useful in this conversion, particularly DBU, potassium carbonate and mixtures thereof. Preferably the base used is an alkali base.

In step (b) above, the contacting of A5 with a compound of formula BC8 to provide a compound of formula ABC1 will generally take place in an organic solvent in the presence of a promoter. A variety of solvents are useful such as ether (e.g., diethyl ether, tetrahydrofuran), MTBE, IPE, diglyme, toluene, DCM, DCE and mixtures thereof. In one group of embodiments, the solvent is selected from diethyl ether, MTBE, IPE, diglyme, toluene, DCM and mixtures thereof. In one group of embodiments, the solvent is a mixture of 0-20% toluene or DCM in MTBE. In other embodiments, the solvent is a mixture of about 15-25% toluene in MTBE, more preferably about 20% toluene in MTBE. The promoters used in this group of embodiments are selected from trialkylsilyls, trifluoromethanesulfonates, and mixtures of trialkylsilyls and trifluoromethanesulfonates. In one group of embodiments, the promoter is trimethylsilyl trifluoromethanesulfonate (TMSOTf), triethylsilyl trifluoromethanesulfonate (TESOTf), tert-butyldimethylsilyl trifluoromethanesulfonate (TBSOTf), trifluoromethanesulfonic acid (TfOH) and mixtures thereof. The collective individual trialkylsilyl triflates (e.g., TMSOTf, TESOTf and TBSOTf) or mixtures thereof are also referred to herein as 'trialkylsilyls'. Example 1 provides an exemplary procedure for the preparation of ABC1. One of skill in the art will understand that other leaving groups may be used instead of the trichloroacetimidate group of compound A5. One of skill in the art will understand that the reaction with BC8 to prepare ABC1 may be carried out under other conditions depending on the choice of the leaving group.

ABC1 is then converted to ABCDE4 via a series of steps as follows. (1) Initially ABC1 is converted to a ketal-hydrolysed product ABC2 in the presence of a promoter, an organic solvent, a base and an acylating agent. Generally the reactions are carried out at about ambient temperature (e.g., from 20° C. to 30° C.), optionally at elevated temperatures. Suitable promoters include trialkylsilyls, trifluoromethanesulfonates, and mixtures of trialkylsilyls and trifluoromethanesulfonates. An exemplary ketal hydrolysis and anomeric acylation is provided in Example 2. (2) The acetyl group at the anomeric position in ABC2 is cleaved in the presence of a base and an aprotic solvent to provide compound ABC3. Examples of aprotic solvents include toluene, xylenes, THF, EA, DCM, DCE and the like. An exemplary acetyl group cleavage is described in Example 3. (3) A leaving group is introduced at the anomeric position of ABC3 to provide compound ABC4. Examples of suitable leaving groups include halogens, activated esters, acetimidates or the like. Generally the reaction is carried out in an aprotic solvent. Examples of aprotic solvents include toluene, xylenes, THF, EA, DCM, DCE and the like. An exemplary introduction of a trichloroacetimidate group (TCA) leaving group is provided in Example 4.

(4) A thio-donor compound ABC5 is generated from ABC4 by reaction of ABC4 with a thiol in the presence of a promoter in an organic solvent. Generally the reaction is carried out in an aprotic solvent. Examples of aprotic solvents include toluene, xylenes, THF, EA, DCM, DCE and the like. Suitable promoters include trialkylsilyls, trifluoromethanesulfonates, and mixtures of trialkylsilyls and trifluoromethanesulfonates. An exemplary introduction of a thiophenyl group is described in Example 4. Generally the reaction mixture includes a base. Examples of bases include organic bases such as triethylamine, diisopropylamine, diisopropylethylamine and the like, or inorganic bases such as potassium carbonate, sodium carbonate, cesium carbonate and the like. One of skill in the art will understand that the introduction of a thio-donor moiety is possible under various conditions and depends on the leaving group present in the compound.

(5) The thio donor compound ABC5 is reacted with an acceptor compound such as DE4 to obtain an oligosaccharide ABCDE1. The reaction is carried out in the presence of a radical initiator and/or a promoter in an organic solvent. Generally the reaction is carried out in an aprotic solvent. Examples of aprotic solvents include toluene, xylenes, THF, EA, DCM, DCE and the like. The reaction is generally carried out at a temperatures ranging from about −30° C. to about 40° C. Suitable promoters include trialkylsilyls, trifluoromethanesulfonates, and mixtures of trialkylsilyls and trifluoromethanesulfonates. Non-limiting examples of radical initiators include N-iodosuccinimide, N-bromosuccinimide and the like. An exemplary reaction between a donor and an acceptor compound is shown in Example 5. One of skill in the art will understand that the donor-acceptor reaction is possible under various conditions and depends on the thio-donor moiety and the acceptor moiety present in the compounds.

The conversion of ABCDE1 to ABCDE5 is achieved as follows. (6) The ester group in ABCDE1 is cleaved in the presence of a peroxide and a base in an aprotic solvent to provide ABCDE2. Examples of aprotic solvents include toluene, xylenes, THF, EA, DCM, DCE and the like. The reaction is generally carried out initially at temperatures below 10° C., then warmed to ambient temperature (e.g., 20° C. to 30° C.). Example 6 provides an exemplary procedure for ester cleavage in an oligosaccharide. (7) ABCDE2 is then O-sulfated in the presence of a base to provide ABCDE3. The reaction is generally carried out in an aprotic solvent by introduction of sulfate groups using a sulfating reagent, followed by addition of a base to introduce counterions for the sulfate groups. Example 7 provides an exemplary procedure for introduction of sodium sulfate groups. (8) The Cbz protecting group in ABCDE3 is removed under suitable conditions to provide ABCDE4. In some cases, hydrogenation is used which also reduces the azido groups to amine groups. The hydrogenation is typically carried out at ambient temperatures (e.g., 20° C. to 30° C.) for a period of 1-5 days, preferably 1-3 days. Example 8 provides an exemplary procedure for conversion of ABCDE3 to ABCDE4.

ABCDE4, prepared as described above, is used in the methods provided herein. In one aspect, provided herein is a process for preparing Fondaparinux sodium comprising converting a compound of formula ABCDE4

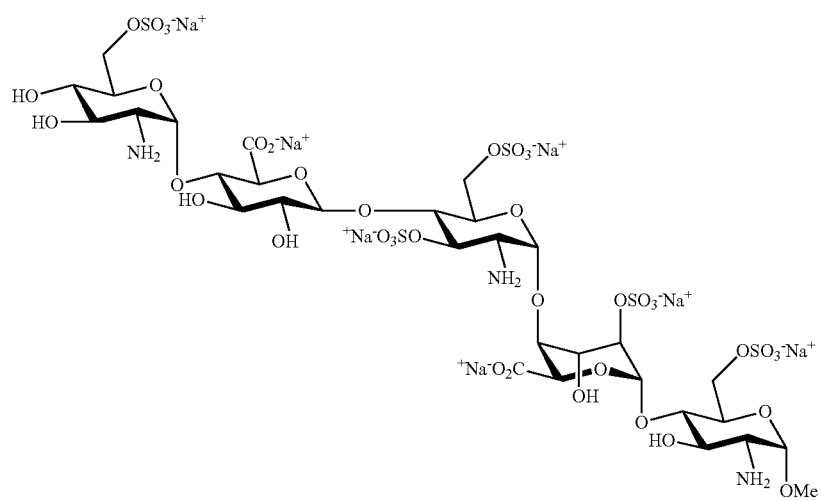

ABCDE4 to Fondaparinux sodium:

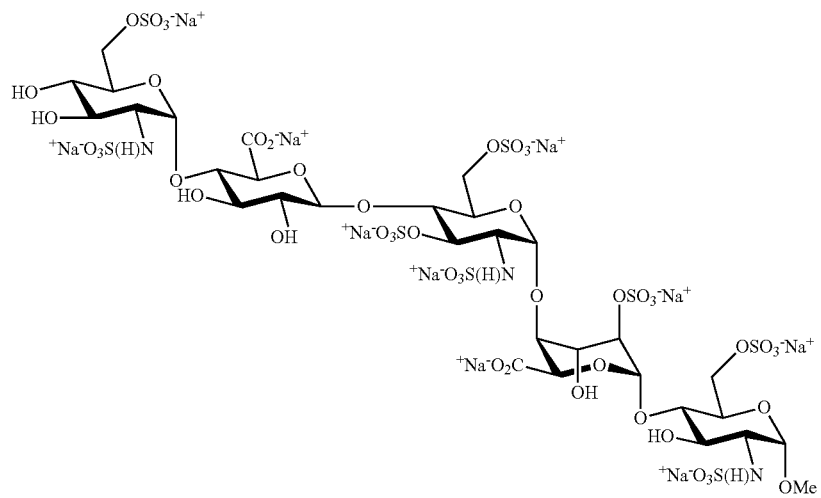

Fondaparinux sodium wherein the conversion is conducted at a reaction pH of no more than about 9.0.

In one group of embodiments, the conversion is a sulfation reaction. In one group of embodiments, the conversion is conducted at a reaction pH of about 7.0 to 9.0, about 7.5 to 9.0, about 8.5 to 9.0, preferably at about 8.0 to 9.0. In another group of embodiments, the conversion is conducted at a reaction pH of about 7.0 to 8.5, or about 7.5 to 8.5.

In one group of embodiments, the conversion is conducted in the presence of a sulfating agent. In group of embodiments, the conversion is conducted in the presence of a sulfur trioxide-amine complex. The sulfur trioxide-amine complex is generally selected from aromatic or alkylamine sulfur trioxide complexes. In one group of embodiments, the sulfur-trioxide amine complex is selected from the group consisting of sulfur trioxide-pyridine complex, sulfur trioxide-trimethylamine complex, sulfur trioxide-triethylamine complex, sulfur trioxide-dimethylethylamine complex, sulfur trioxide-dimethylaniline complex, and mixtures thereof. In a select embodiment, the sulfur trioxide-amine complex is sulfur trioxide-trimethylamine complex.

In one case, Fondaparinux sodium that is formed using the process described above contains less than about 1% of a mixture of ABCDE4-4S-1, ABCDE4-4S-2, ABCDE4-4S-3, ABCDE4-4S-4, ABCDE4-4S-5, ABCDE4-4S-6, when the conversion is carried out with an ABCDE4 solution and at a reaction pH of about 8.0 to 9.0, where ABCDE4-4S-1, ABCDE4-4S-2, ABCDE4-4S-3, ABCDE4-4S-4, ABCDE4-4S-5, ABCDE4-4S-6 are as described in the summary of the invention.

In some embodiments of the process described above, the compound of formula ABCDE4 is purified with activated charcoal prior to the conversion step. In some of such embodiments, the ABCDE4 contacted with activated charcoal is in the form of an aqueous solution. In some of such embodiments, the contacting of ABCDE4 solution with activated charcoal is carried out at ambient temperature (e.g., 20° C. to 30° C.). In alternate embodiments, the contacting of ABCDE4 solution with activated charcoal is carried out at elevated temperature (e.g., a temperature above the ambient temperature and up to the boiling point of the solvent).

In a second aspect, provided herein is a process of preparing Fondaparinux sodium comprising converting a compound of formula ABCDE4

ABCDE4

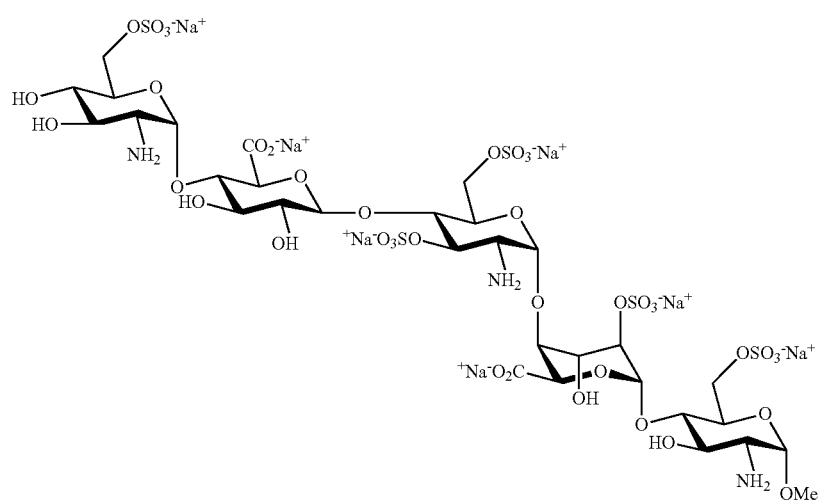

to Fondaparinux sodium:

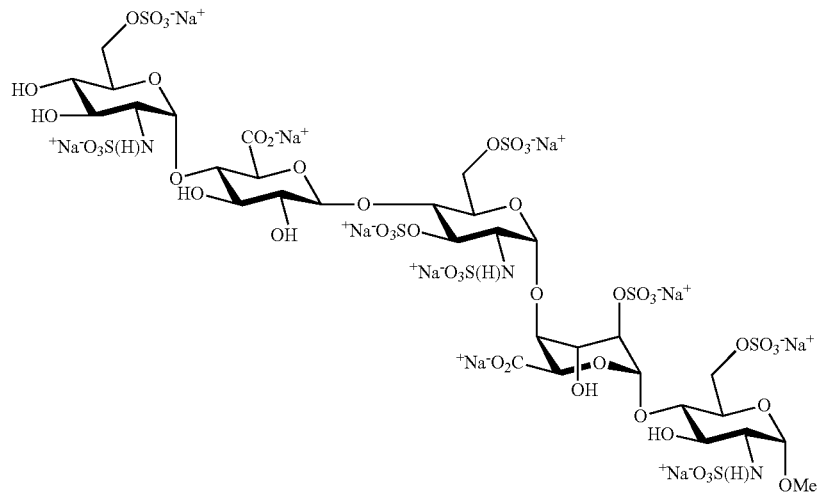

Fondaparinux sodium in the presence of a sulfur trioxide trialkylamine complex.

In a group of embodiments for the process described above, the sulfur trioxide-trialkylamine complex is selected from the group consisting of sulfur trioxide-trimethylamine complex, sulfur trioxide-triethylamine complex and mixtures thereof, preferably the sulfur trioxide-trialkylamine complex is sulfur trioxide-trimethylamine complex.

In one group of embodiments, the reaction conducted in the presence of a sulfur trioxide-trialkylamine complex is a sulfation reaction. In one group of embodiments, the reaction is conducted at a reaction pH of about 7.0 to 9.0, about 7.5 to 9.0, about 8.5 to 9.0, preferably at about 8.0 to 9.0. In another group of embodiments, the reaction is conducted at a reaction pH of about 7.0 to 8.5, or about 7.5 to 8.5.

In a third aspect, provided herein is a process of preparing Fondaparinux sodium comprising converting a compound of formula ABCDE4

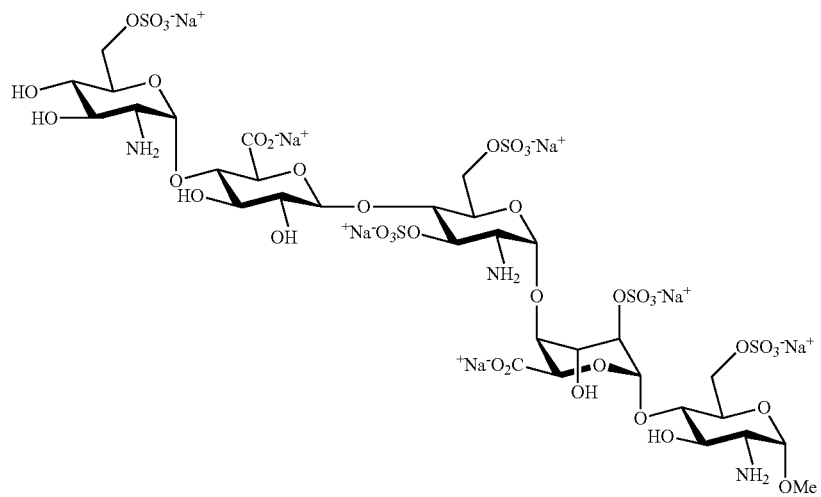

ABCDE4 to Fondaparinux sodium:

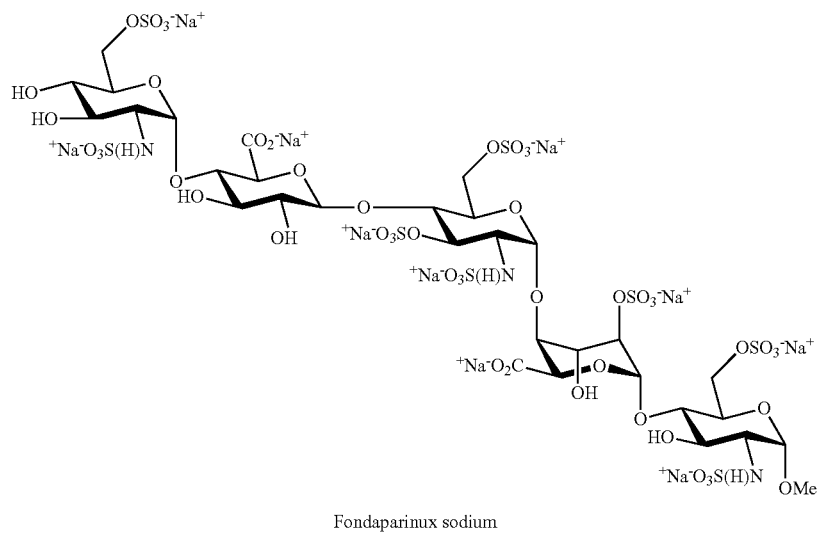

Fondaparinux sodium at a reaction pH of about 8.0 to 9.0 in the presence of a sulfur trioxide-trimethylamine complex.

EXAMPLES

The following examples are presented to describe the invention in further detail. However, the present invention is by no means restricted to the specific embodiments described herein. The following abbreviations are used in the specification, and examples: DCM is dichloromethane; EA is ethyl acetate; THF is tetrahydrofuran; MTBE is methyl tert-butyl ether; DMAc is dimethylacetamide; OTCA is a trichloroacetimidate group; DCE is dichloroethane; IPE is isopropyl ether; CBz is carboxybenzyl, a carbamate protecting group. Compound BC8 can be prepared according to U.S. application publication no. 20120083594. Compound A4 can be prepared according to procedures in *J. Am Chem Soc.*, 2005, 127, 3767-3773; or *Tetrahedron: Asymmetry*, 2005, 16(2), 411-424.

Example 1

Preparation of ABC1

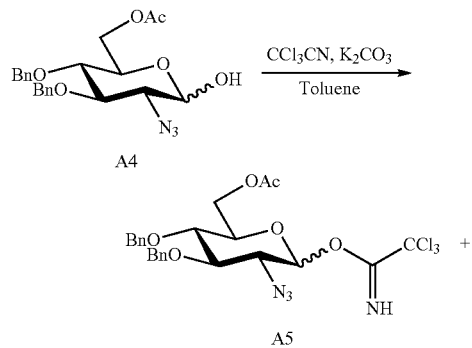

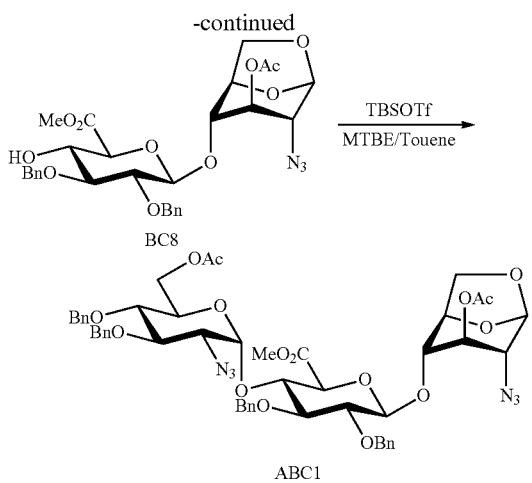

A4 to A5

A four-necked round bottom flask was equipped with a mechanical stirrer and a thermometer. To the flask was added A4 (32 g, 75 mmol, 1.4 equiv), toluene (64 mL), $K_2CO_3$ (52 g, 374 mmol, 7.0 equiv), and $CCl_3CN$ (37 mL, 374 mmol, 7.0 equiv) at 20-30° C. under nitrogen. The mixture was stirred at 20-30° C. for 4 hr. The mixture was filtered and the filtered cake was washed with toluene (64 mL). The filtrate and washing were combined to afford A5 in toluene solution. After being cooled to no more than −10° C., the A5/toluene solution was ready to be used.

BC8 to ABC1

A four-necked round bottom flask was equipped with a mechanical stirrer and a thermometer. To this flask was added BC8 (32 g, 53 mmol, 1 equiv) and MTBE (576 mL) at 20-30° C. under nitrogen. The mixture was heated to no more than 45° C. for dissolution. After being cooled to 20-30° C., 3 Å molecular sieves (15 g) were added to the mixture and the resulting mixture was stirred at this temperature for 2 hr. The mixture was then cooled to −35 to −25° C. TBSOTf (5 mL, 21 mmol, 0.4 equiv) was added at −35 to −25° C., and the mixture was stirred at this temperature for about 15 min. The resulting mixture containing BC8 and 3 Å molecular sieves in MTBE was ready to be used.

To the flask containing A5/toluene solution was added into the mixture containing BC8 and 3 Å molecular sieves in MTBE over 30 min while maintaining temperature at −35 to −25° C. The mixture was stirred at −35 to −25° C. for 1 hr. Triethylamine (23 mL, 160 mmol, 3 equiv) and $Ac_2O$ (5 mL, 53 mmol, 1 equiv) were successively added at −35 to −25° C. The mixture was heated to about 50° C. and stirred for 6 hr. The mixture was filtered and the filtered cake was washed with MTBE (64 mL). The filtrate and washing were combined and concentrated to afford crude ABC1 solution. Crude ABC1 solution was purified using silica gel column chromatography; eluting solvent: EtOAc/n-heptane (first eluting solvent is 1:4 and then 2:3) and then concentrated to afford ABC1 in EtOAc/n-heptane (1/1) solution (50 g, 88%).

Example 2

Preparation of ABC2

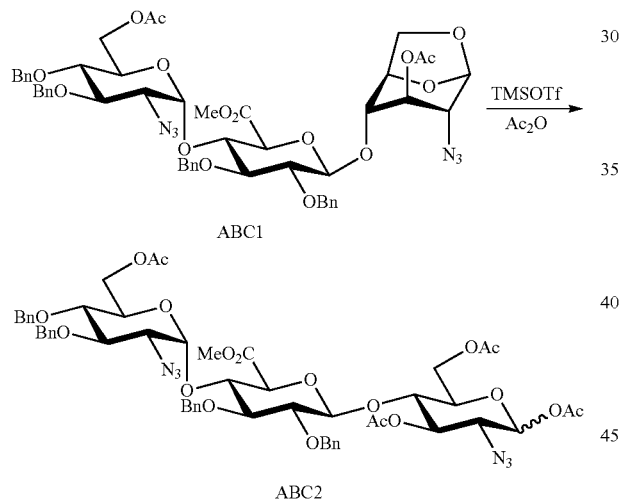

A three-necked round bottom flask was equipped with a mechanical stirrer and a thermometer. To the flask was added the previously reserved ABC1 in EtOAc/n-heptane solution (162 mL, 1/1 (v/v)) at 20-30° C. under nitrogen. After the mixture was cooled to 0-10° C., $Ac_2O$ (16.3 g, 0.16 mol, 3.0 equiv) and TMSOTf (3.6 g, 0.02 mol, 0.3 equiv) were successively added at this temperature. The mixture was stirred at 0-10° C. for not less than 10 hr. Triethylamine (45 mL, 0.27 mol, 6.0 equiv) was slowly added at 0-10° C. The mixture was stirred at 0-10° C. for 1 hr. 20% $NaCl_{(aq)}$ (64 mL, 2 vol) was slowly added at 0-10° C. The mixture was stirred for 2 hr. The separated aqueous portion was discarded. The separated organic portion containing ABC2 in EtOAc/n-heptane (1/1 (v/v)) solution was ready to be used in the next step.

Example 3

Preparation of ABC3

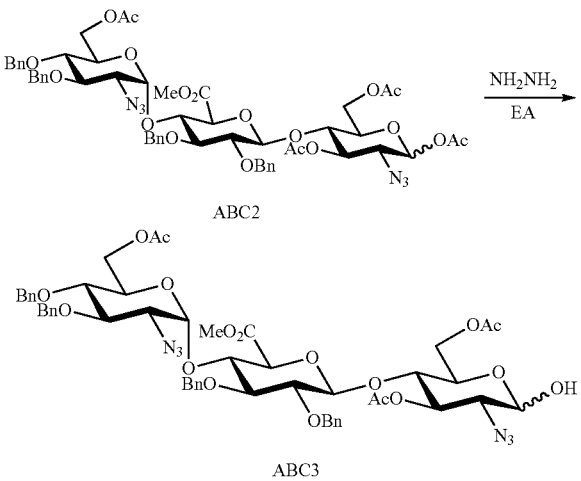

A three-necked round bottom flask was equipped with a mechanical stirrer and a thermometer. To the flask was added the previously reserved ABC2 in EtOAc/n-heptane (1/1 (v/v)) solution at 20-30° C. under nitrogen. $H_2NNH_2$—$H_2O$ (3.8 g, 80 mmol, 1.4 equiv) was added at 20-30° C., and the mixture was stirred at this temperature for 3 hr. A 5% solution of $NaCl_{(aq)}$ (160 mL) was added at 20-30° C., and the mixture was stirred at this temperature for 1 hr. The stirring was stopped for phase separation. The separated aqueous phase was discarded. The organic and emulsion portions were combined and concentrated to afford crude ABC3 in EtOAc/n-heptane solution. Crude ABC3 solution was purified with column chromatography (silica gel; eluting solvent: acetone/toluene (containing 0.05% (v/v) of $Et_3N$, 5/95 (v/v))) and then concentrated to afford ABC3 in toluene solution (44 g, 94%).

Example 4

Preparation of ABC5

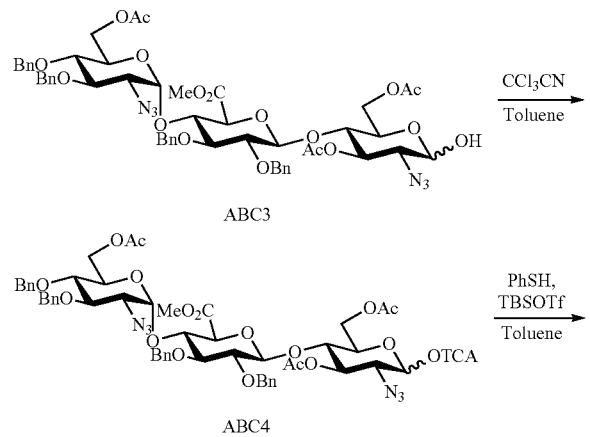

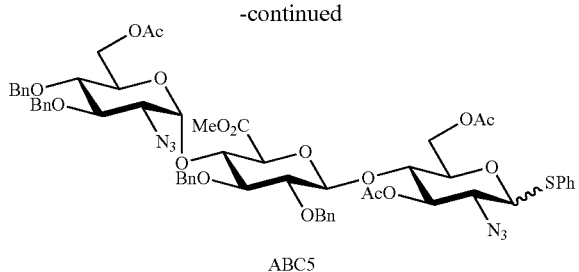

ABC5

ABC3 to ABC4

A four-necked round bottom flask was equipped with a mechanical stirrer and a thermometer. To the flask was added ABC3/toluene solution (about 96 mL, 3 vol) at 20-30° C. under nitrogen. K₂CO₃ (74 g, 0.53 mol, 10 equiv) and CCl₃CN (77 g, 0.53 mol, 10 equiv) were successively added at 20-30° C. The mixture was stirred at 20-30° C. for not less than 4 hr. The mixture was filtered and the filtered cake was washed with toluene (64 mL, 2 vol). The filtrate and washing were combined to afford ABC4 in toluene solution. After being cooled to no more than −5° C., the ABC4/toluene solution (about 160 mL, 5 vol) was ready to be used.

ABC4 to ABC5

A four-necked round bottom flask was equipped with a mechanical stirrer and a thermometer. To the flask was added thiophenol (24 g, 0.2 mmol, 4 equiv) and toluene (260 mL) at 20-30° C. under nitrogen. The mixture was cooled to −20 to −10° C. TBSOTf (21 g, 0.08 mol, 1.5 equiv) was added at −20 to −10° C. The resulting mixture containing thiophenol and TBSOTf in toluene was ready to be used.

To the flask containing ABC4 solution was added the mixture containing thiophenol and TBSOTf in toluene over 30 min while maintaining temperature at −20 to −10° C. The mixture was stirred at −20 to −10° C. for 2 hr. Et₃N/toluene (15 mL/65 mL) was slowly added over about 30 min while maintaining temperature no more than −5° C. The mixture was stirred at no more than −5° C. for 30 min. The mixture was concentrated to afford crude ABC5 solution in toluene. ABC5 solution was purified with column (silica gel; eluting solvent: EtOAc/toluene (containing 0.05% (v/v) of Et₃N, 2/98, (v/v))) to afford ABC5 in toluene solution (42 g, 88%).

Example 5

Preparation of ABCDE1

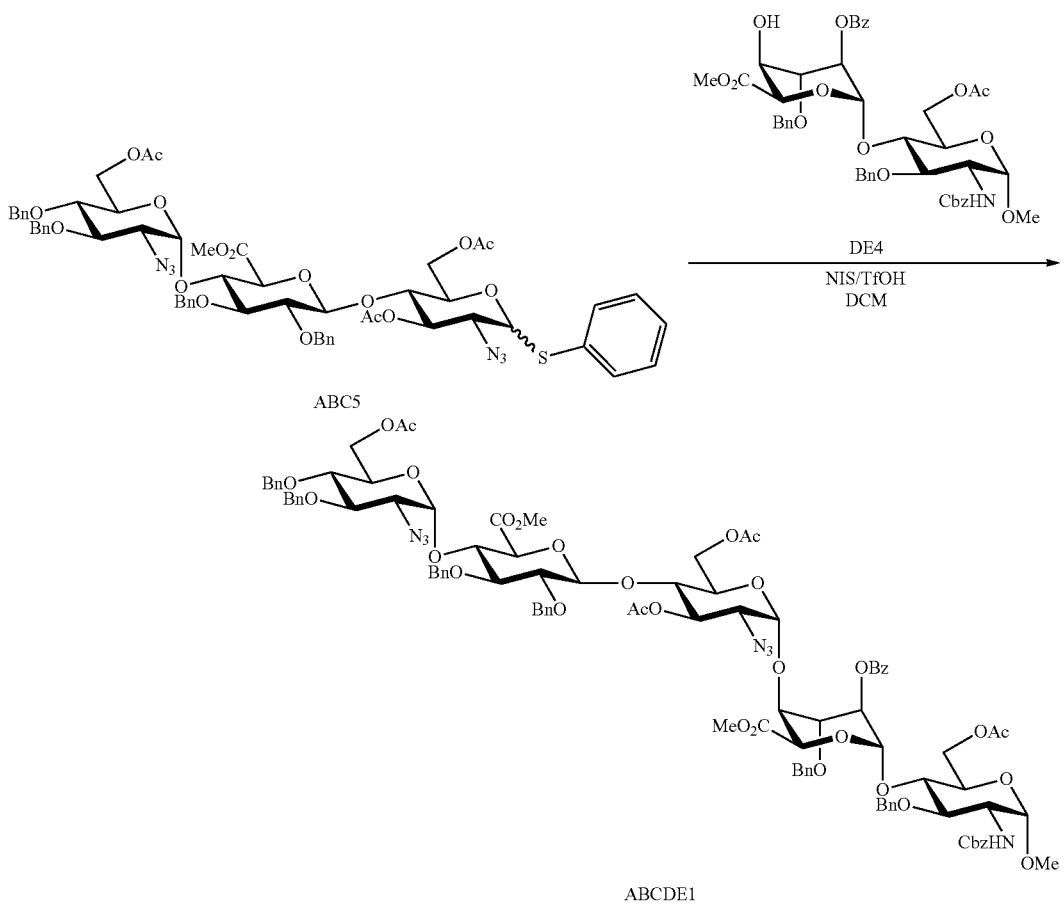

ABC5 (35 g, 0.03 mol, 1.0 equiv), DE4 (28 g, 0.033 mol, 1.1 equiv), and DCM (700 g,) were added into a four-necked round bottom flask equipped with a mechanical stirrer and a thermometer at 20-40° C. under nitrogen. The mixture was stirred at 20-40° C. for 30 min to obtain a homogeneous solution. 3 Å molecular sieves (35 g) was added at 20-40° C., and the mixture was stirred at this temperature for 1 hr.

After the mixture was cooled to −30 to −20° C., N-iodosuccinimide (NIS) (10.2 g, 1.5 equiv, 0.045 mol) was added at this temperature and stirred for 15 min. TfOH (1.8 g, 0.012 mol, 0.4 equiv) in DCM (10 mL) was slowly added at −30 to −20° C., and the mixture was stirred at this temperature for 2 hr. Et$_3$N (6.1 g, 0.06 mol, 2 equiv) was added at −30 to −20° C., and the mixture was stirred at this temperature for 30 min. The mixture was filtered through a celite pad, and the filtered cake was washed with DCM (140 mL). The combined filtrate and washing was added 30% Na$_2$S$_2$O$_3$.5H$_2$O$_{(aq)}$ (105 mL, 3 vol) at 20-40° C. After the mixture was stirred at 20-40° C. for 1 hr, the stirring was stopped for about 5 min to effect phase separation. The separated aqueous portion was discarded. The separated organic portion was concentrated to afford crude ABCDE1 solution in DCM. Crude ABCDE1 solution was purified with column chromatography (silica gel; eluting solvent: EtOAc/toluene (containing Et$_3$N (0.1% (v/v)) 1/9 (v/v)) to provide a solution of ABCDE1 in toluene solution.

ABCDE1 in toluene solution (about 105 mL) was added into a four-necked round bottom flask equipped with a mechanical stirrer and a thermometer under nitrogen. After the mixture was heated to 35-45° C., IPA (105 mL) and n-heptane (105 mL) were sequentially added at this temperature. ABCDE1 seed (0.035 g) was added at 35-45° C., and the mixture was stirred at this temperature for 1 hr. After n-heptane (175 mL) was added at 35-45° C., the mixture was cooled to 15-25° C. and stirred for 1 hr. The mixture was filtered and the filtered cake was washed with n-heptane (70 mL). The wet cake was dried at no more than 60° C. to afford ABCDE1 (39 g, 65%) as a white solid.

Example 6

Preparation of ABCDE2

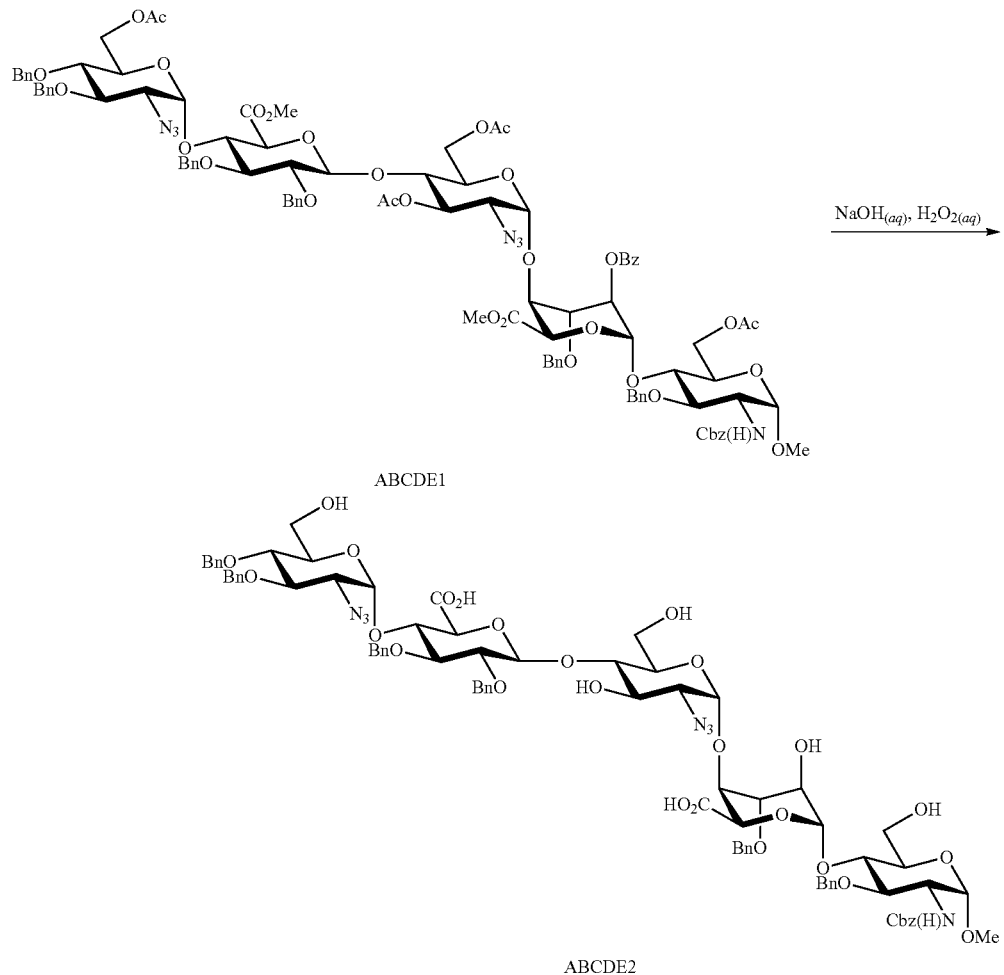

THF (250 mL) and ABCDE1 (50 g, 26.4 mmol, 1.0 equiv) were charged into a four-necked round bottom flask at 20-40° C. under nitrogen. The mixture was cooled to 10° C., and 35% H$_2$O$_{2(aq)}$ (102.5 mL, 1161 mmol, 44 equiv) was added at this temperature. 2N NaOH$_{(aq)}$ (356 mL, 712.4 mmol, 27 equiv) was added at 10° C. The mixture was heated to 20-30° C. and stirred for 48 hr. The stirring was stopped for about 5 min to affect phase separation. The separated organic portion was saved, and the separated aqueous portion was discarded. The reserved organic portion was added 30% Na$_2$S$_2$O$_3$.5H$_2$O$_{(aq)}$ (250 mL, 5 vol), and the mixture was stirred for about 5 min. The stirring was stopped for about 5 min to affect phase separation. The separated organic portion was saved, and the separated aqueous portion was discarded. The reserved organic portion was added 30% Na$_2$S$_2$O$_3$.5H$_2$O$_{(aq)}$ (250 mL, 5 vol), and the mixture was stirred for about 5 min. The stirring was stopped for about 5 min to affect phase separation. The separated organic portion was saved, and the separated aqueous portion was discarded. The reserved organic portion was added $H_2O$ (500 mL, 10 vol), and 1N $HCl_{(aq)}$ (45 mL, 0.9 vol) was added till pH of the mixture reached 4-5. Acetone (250 mL, 5 vol) was added and the mixture was concentrated at 35-60° C. till volume reached about 700 mL. 1N $HCl_{(aq)}$ (5 mL) was added till pH of the mixture reached 2.5-3.5. After being stirred at 20-30° C. for 30 min, the mixture was filtered and the filtered cake was washed with $H_2O$ (250 mL). The wet cake was dried at no more than 60° C. to afford ABCDE2 as white solid (38.4 g, 82% yield).

Example 7

Preparation of ABCDE3

ABCDE2 (8 g, 1.0 equiv, 5.02 mmol), $SO_3$-TMA complex (38.4 g, 55 equiv, 275.92 mmol), and DMAc (88 mL) were added into a round bottom flask equipped with a mechanical stirrer and a thermometer under nitrogen at 20-40° C. The slurry mixture was heated to 55-65° C. and stirred for 6 hr. After being cooled to no more than 10° C., to the mixture was added 8% $NaHCO_{3(aq)}$ (40 mL) at no more than 30° C. The mixture was filtered and the filtered cake was washed with DMAc (96 mL). After the combined filtrate and washing was cooled to no more than 10° C., water (88 mL) was slowly added while maintaining temperature at 30° C. A mixture containing crude ABCDE3 DMAc/water solution was thus obtained. ABCDE3 was purified with HP20SS resin by eluting solvent via $NaCl_{(aq)}$ (10%) and then MeOH and then solvent exchanged with water to afford ABCDE3 aqueous solution.

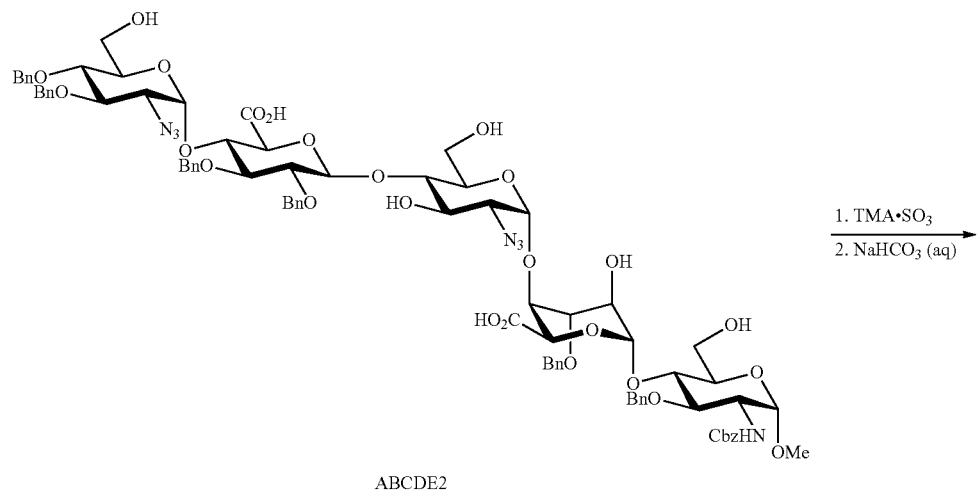

ABCDE2

1. TMA•SO$_3$
2. NaHCO$_3$ (aq)

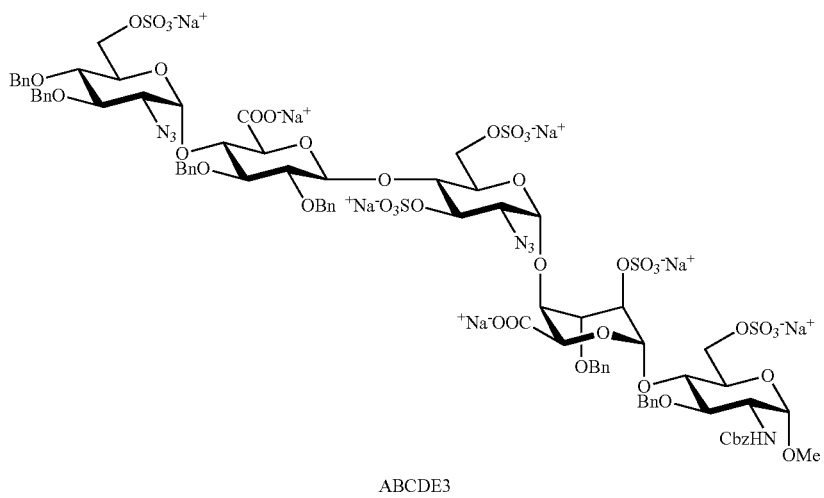

ABCDE3

Example 8

Preparation of ABCDE4

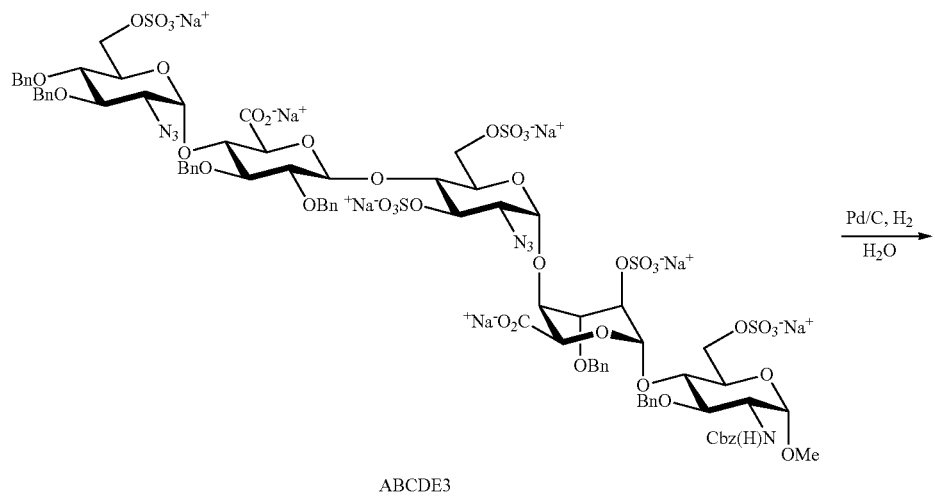

ABCDE3

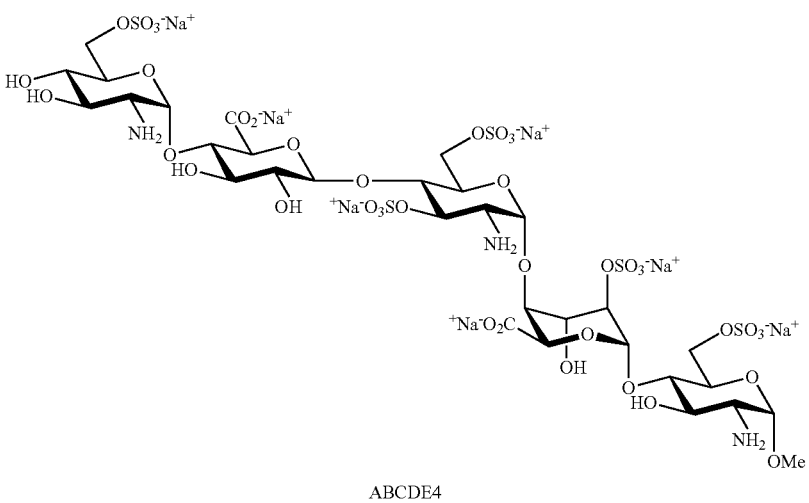

ABCDE4

ABCDE3 aqueous solution (based on 8 g of ABCDE2), and 10% Pd/C (3.2 g, 40% wt) were added into an autoclave at 20-30° C. The mixture was exposed to hydrogen (0-0.5 kg, gauge pressure) at 20-30° C. for 48 hr. The mixture was filtered through a celite pad, and the filtered cake was washed with water (32 mL). After the combined filtrate and washing was added activated charcoal (1.6 g,) at 20-30° C., the mixture was stirred at this temperature for 3 hr. The mixture was filtered through a celite pad, and the filtrate was saved. The reactor was rinsed with water (32 mL), and the solution was filtered through a 0.2 micrometer filter. The two filtrates were combined to afford a ABCDE4 aqueous solution.

Example 9

Preparation of Fondaparinux

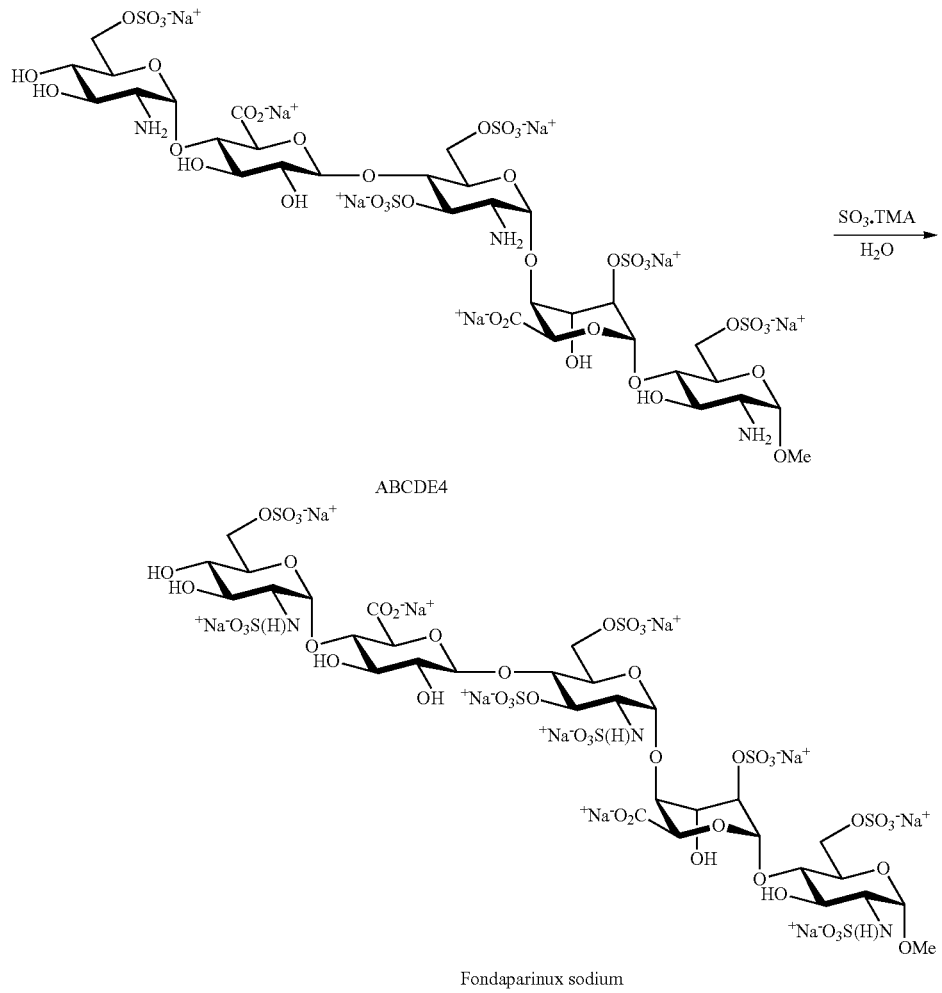

ABCDE4 aqueous solution (based on 8 g of ABCDE2) was added into a round bottom flask equipped with a mechanical stirrer and thermometer at 20-40° C. The mixture was added 1N $HCl_{(aq)}$ till pH reached 8-9. After $SO_3$.TMA (23.04 g, 33 equiv, 165.5 mmol) was added at 20-40° C., the mixture was heated to 40-50° C. and stirred for 10 hr. The mixture was cooled to no more than 10° C. The mixture was filtered and the filtered cake was washed with water (32 mL). The filtrate was added 1N $NaOH_{(aq)}$ till pH reached 9-10. The mixture was heated to 45-55° C. and stirred for 20 hr. The mixture was cooled to no more than 30° C. A mixture containing crude Fondaparinux sodium aqueous solution was thus obtained.

Crude Fondaparinux sodium aqueous solution (2.4 g) was purified with Q Sepharose Fast Flow resin (QSFF) (190 mL) using the eluting solvent via 0.4M $NaCl_{(aq)}$, 0.8M $NaCl_{(aq)}$ and 2M $NaCl_{(aq)}$ to afford Fondaparinux sodium solution. Fondaparinux sodium was desalted by 0.1 m² of 1 kDa regenerous cellulose (RC) membrane using Tangential Flow Filtration (TFF) and then lyophilized to afford Fondaparinux (2.2 g, 80%).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A process of preparing Fondaparinux sodium comprising converting a compound of formula ABCDE4

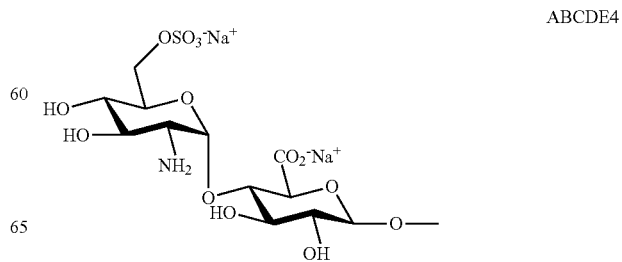

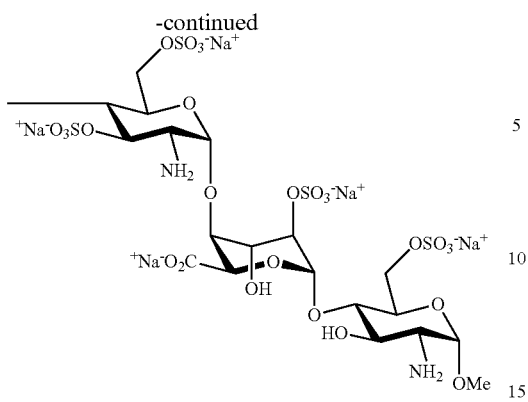

to Fondaparinux sodium:

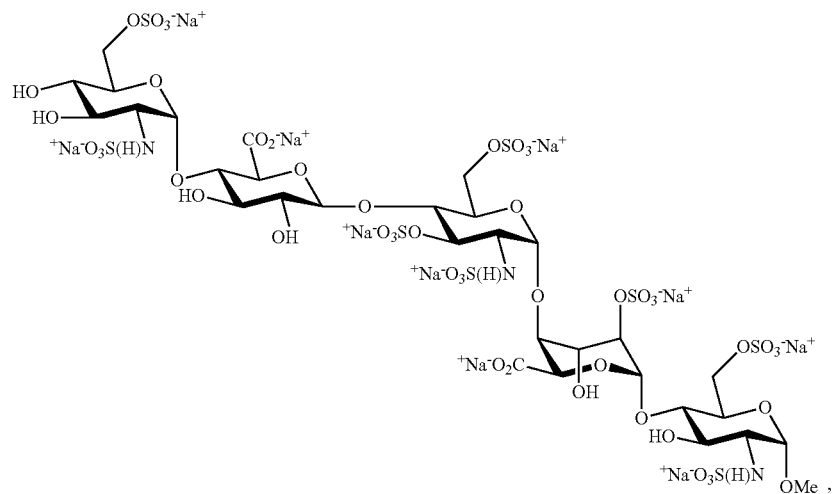

Fondaparinux sodium wherein the compound ABCDE4 is in a solution having a pH 8.0 to 9.0 prior to initiating the conversion; and the conversion is conducted at a reaction pH of less than 9.0 in the presence of a sulfur trioxide-trimethylamine complex.

2. A process of claim 1, wherein the conversion is conducted at a reaction pH of 7.5 to 8.5.

3. A process of claim 1, wherein Fondaparinux sodium that is formed contains less than about 1% of a mixture of ABCDE4-4S-1, ABCDE4-4S-2, ABCDE4-4S-3, ABCDE4-4S-4, ABCDE4-4S-5, ABCDE4-4S-6

ABCDE4-4S-1

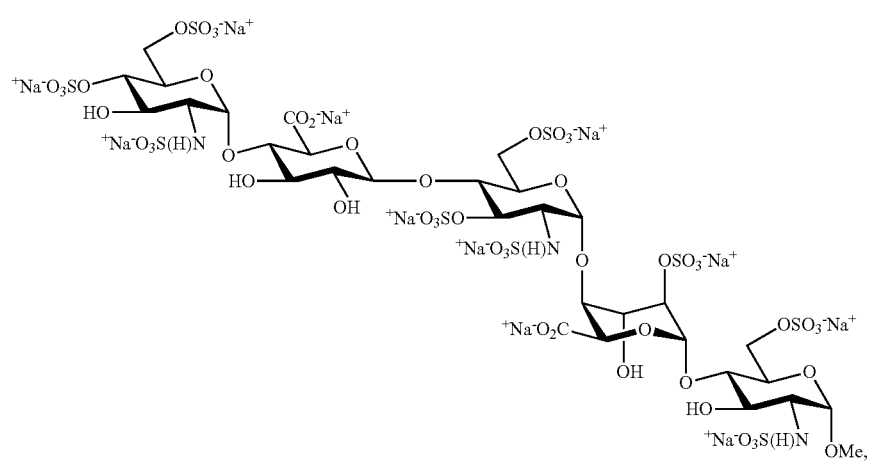

ABCDE4-4S-2
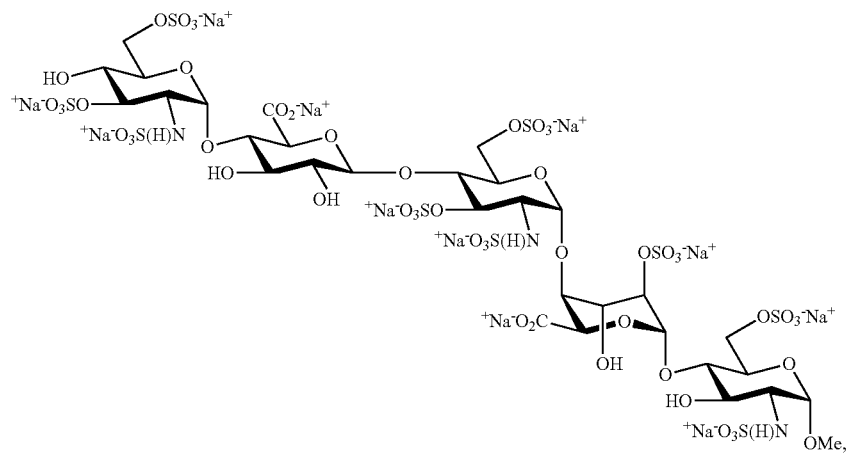
ABCDE4-4S-3
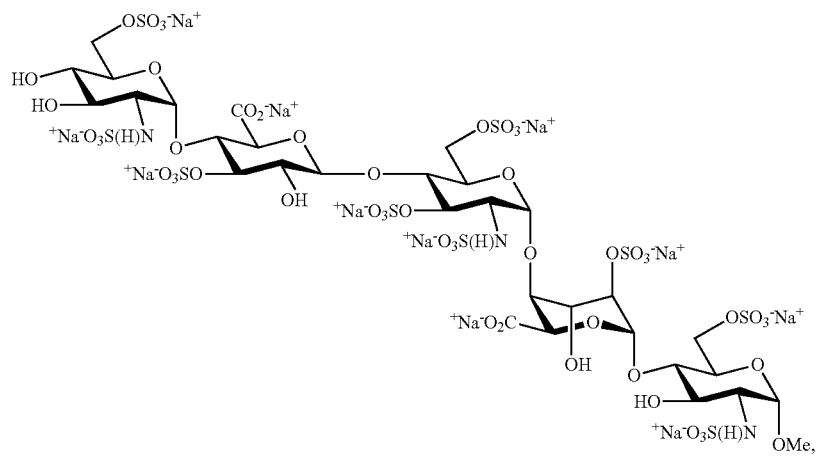
ABCDE4-4S-4
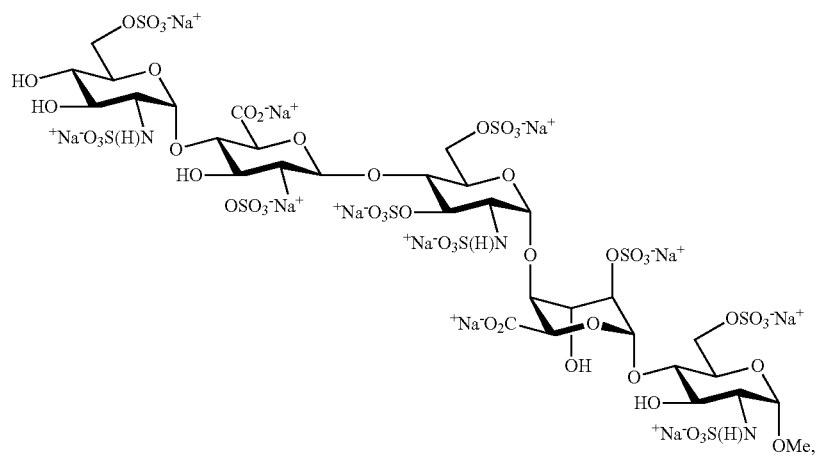

-continued
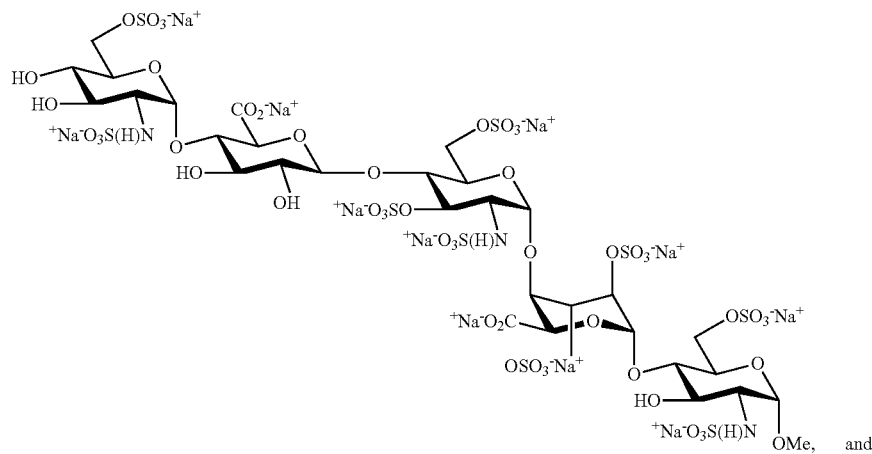
ABCDE4-4S-5
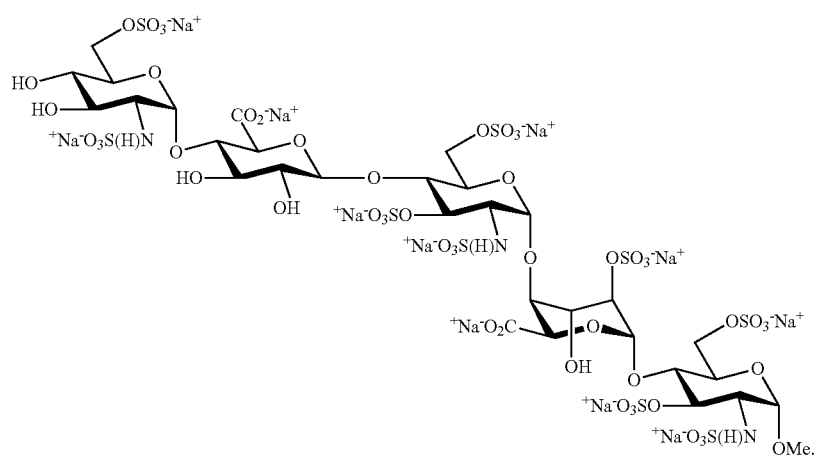
ABCDE4-4S-6
4. A process of claim 1, wherein the compound of formula ABCDE4 is purified with activated charcoal prior to the conversion.
* * * * *